(12) United States Patent
Rabiner et al.

(10) Patent No.: US 8,523,901 B2
(45) Date of Patent: Sep. 3, 2013

(54) APPARATUS AND METHODS FOR ATTACHING SOFT TISSUE TO BONE

(75) Inventors: Robert A. Rabiner, Tiverton, RI (US); Andrew Green, Providence, RI (US)

(73) Assignee: IlluminOss Medical, Inc., East Providence, RI (US)

( * ) Notice: Subject to any disclaimer, the term of this patent is extended or adjusted under 35 U.S.C. 154(b) by 1111 days.

(21) Appl. No.: 11/893,075

(22) Filed: Aug. 14, 2007

(65) Prior Publication Data

US 2009/0048629 A1    Feb. 19, 2009

(51) Int. Cl.
*A61B 17/04* (2006.01)
*A61M 29/00* (2006.01)

(52) U.S. Cl.
USPC .......................................... 606/232; 606/192

(58) Field of Classification Search
USPC ................. 606/232, 300–321, 191, 192, 198, 606/151, 195, 194; 604/104, 90, 102.01, 604/93.01, 174, 164.01, 175, 907, 912, 915, 604/916, 918, 96.01, 103, 103.07; 128/836; 623/17.12
See application file for complete search history.

(56) References Cited

U.S. PATENT DOCUMENTS

| | | | | |
|---|---|---|---|---|
| 5,037,422 A | | 8/1991 | Hayhurst et al. ................ 606/72 |
| 5,779,672 A | * | 7/1998 | Dormandy, Jr. ........... 604/99.04 |
| 5,820,586 A | * | 10/1998 | Booth et al. .................... 604/509 |
| 6,027,523 A | * | 2/2000 | Schmieding ................... 606/232 |
| 6,045,573 A | | 4/2000 | Wenstrom, Jr. et al. ....... 606/232 |
| 6,117,161 A | | 9/2000 | Li et al. .......................... 606/232 |
| 6,443,988 B2 | | 9/2002 | Felt et al. .................... 623/17.12 |
| 6,533,761 B2 | * | 3/2003 | Bertoch et al. ................. 604/174 |
| 6,547,800 B2 | | 4/2003 | Foerster et al. ............... 606/151 |
| 6,582,453 B1 | | 6/2003 | Tran et al. ...................... 606/232 |
| 6,652,563 B2 | | 11/2003 | Dreyfuss ........................ 606/232 |
| 6,660,008 B1 | | 12/2003 | Foerster et al. ................. 606/72 |
| 6,899,719 B2 | | 5/2005 | Reiley et al. ................... 606/192 |
| 6,923,824 B2 | | 8/2005 | Morgan et al. ................. 606/232 |
| 7,377,934 B2 | * | 5/2008 | Lin et al. ........................ 606/232 |
| 7,488,320 B2 | | 2/2009 | Middleton |
| 7,491,236 B2 | * | 2/2009 | Cragg et al. ................. 623/17.11 |
| 7,509,175 B2 | * | 3/2009 | Sparks et al. .................. 607/133 |
| 2001/0004710 A1 | | 6/2001 | Felt et al. .................... 623/17.12 |
| 2001/0049531 A1 | | 12/2001 | Reiley et al. ..................... 606/93 |
| 2002/0147496 A1 | * | 10/2002 | Belef et al. ................. 623/17.12 |

(Continued)

OTHER PUBLICATIONS

International Search Report based on PCT/US2008/073016 dated Nov. 14, 2008.

*Primary Examiner* — Corrine M McDermott
*Assistant Examiner* — Christopher L Templeton
(74) *Attorney, Agent, or Firm* — Greenberg Traurig, LLP; David J. Dykeman; Danielle T. Abramson

(57) ABSTRACT

Suture anchors and methods for using the suture anchors for attaching soft tissue, such as ligaments, tendons, and muscles, to bone are disclosed. A suture anchor for attaching soft tissue to bone includes a catheter having an elongated shaft with a proximal end, a distal end, and a longitudinal axis between the proximal and distal ends, wherein the catheter has at least one inner lumen capable of allowing a light curable adhesive to pass through the inner lumen; a balloon portion engaging the distal end of the catheter, wherein the balloon portion expands from a deflated state to an inflated state when a light curable adhesive is delivered to the balloon portion; and at least one suture material for passing through soft tissue to attach the soft tissue to a bone.

15 Claims, 6 Drawing Sheets

(56) References Cited

U.S. PATENT DOCUMENTS

| | | |
|---|---|---|
| 2003/0083662 A1 | 5/2003 | Middleton |
| 2003/0158569 A1* | 8/2003 | Wazne .......................... 606/191 |
| 2004/0010287 A1* | 1/2004 | Bonutti .......................... 606/232 |
| 2004/0097986 A1* | 5/2004 | Adams .......................... 606/151 |
| 2004/0111061 A1* | 6/2004 | Curran .......................... 604/174 |
| 2006/0106361 A1* | 5/2006 | Muni et al. .................... 604/500 |
| 2006/0149280 A1 | 7/2006 | Harvie et al. ................... 606/92 |
| 2006/0253198 A1* | 11/2006 | Myint et al. ................ 623/17.12 |
| 2006/0253200 A1* | 11/2006 | Bao et al. ................... 623/17.12 |
| 2007/0118143 A1 | 5/2007 | Ralph et al. ..................... 606/92 |
| 2007/0198023 A1 | 8/2007 | Sand et al. ...................... 606/92 |
| 2007/0225705 A1 | 9/2007 | Osorio et al. ................... 606/60 |
| 2007/0255287 A1 | 11/2007 | Rabiner .......................... 606/94 |
| 2008/0033480 A1* | 2/2008 | Hardert ......................... 606/200 |
| 2008/0039854 A1 | 2/2008 | Rabiner .......................... 606/92 |
| 2008/0097509 A1* | 4/2008 | Beyar et al. ................... 606/192 |
| 2008/0125784 A1 | 5/2008 | Rabiner et al. ................. 606/92 |
| 2008/0195137 A1* | 8/2008 | Alleyne et al. ................ 606/195 |
| 2009/0204117 A1 | 8/2009 | Middleton |

* cited by examiner

APPARATUS AND METHODS FOR ATTACHING SOFT TISSUE TO BONE

RELATED APPLICATIONS

None.

FIELD

The embodiments disclosed herein relate to medical apparatuses for attaching soft tissue to bone, and more particularly to suture anchors and methods for attaching soft tissue, such as ligaments, tendons, and muscles, to bone.

BACKGROUND

The detachment of soft tissue, such as ligaments, tendons, and muscles, from their associated bones within the body are relatively common injuries. A number of devices and methods have been developed to re-attach soft tissue to bone including, screws, wedges, plugs, nails, pins, staples, cement, and sutures. In certain detachments, it is desirable to anchor one end of a length of suture inside a bone while the other end of the length of suture extends outside of the bone. The free end of the suture may then be used to re-attach the soft tissue to the bone.

Prior techniques for attaching soft tissue to bone are described in U.S. Pat. No. 5,037,422 entitled "Bone Anchor and Method of Anchoring a Suture to a Bone;" U.S. Pat. No. 6,045,573 entitled "Suture Anchor Having Multiple Sutures;" U.S. Pat. No. 6,547,800 entitled "Method and Apparatus for Attaching Connective Tissues to Bone Using a Cortical Bone Anchoring Device;" U.S. Pat. No. 6,582,453 entitled "Method and Apparatus for Attaching Connective Tissues to Bone Using a Suture Anchoring Device;" U.S. Pat. No. 6,660,008 entitled "Method and Apparatus for Attaching Connective Tissues to Bone Using a Suture Anchoring Device;" U.S. Pat. No. 6,923,824 entitled "Apparatus and Method for Securing Suture to Bone;" and U.S. Patent Application No. 2006/0149280 entitled "Surgical Procedures and Instruments."

The prior devices and methods designed for attaching soft tissue to bone present problems to the medical professional and the patient. The anchor may "back out" of the bone implantation site over time, especially in softer bone sites, such as cancellous bone, or in bone tissue that has become compromised, such as in osteoporotic bone sites. Problems associated with the sutures of the prior devices include binding, tangling, inadvertent knotting or twisting, and the inability to maneuver the sutures independently.

Thus, there is a need in the art for an apparatus and method for attaching soft tissue to bone with high pullout resistance in various bone types while controlling the maneuverability and the placement of sutures.

SUMMARY

Suture anchors and methods for using the suture anchors for attaching soft tissue, such as ligaments, tendons, and muscles, to bone are disclosed herein. According to aspects illustrated herein, there is provided a suture anchor for attaching soft tissue to bone that includes a catheter having an elongated shaft with a proximal end, a distal end, and a longitudinal axis therebetween, and at least one inner lumen for a light curable adhesive to pass therethrough; a balloon portion engaging the distal end of the catheter; wherein the balloon portion expands from a deflated state to an inflated state when the light curable adhesive is delivered to the balloon portion; and at least one suture material for passing through soft tissue to attach the soft tissue to a bone.

According to aspects illustrated herein, there is provided a method for using a suture anchor to engage a soft tissue to a bone that includes forming an access hole in a bone, the access hole having a diameter and extending through a cortical bone into a cancellous bone; providing a suture anchor to the access hole, the suture anchor comprising at least one suture material and a balloon portion capable of expanding from a deflated state having a deflated diameter to an inflated state having an inflated diameter when a light curable adhesive is delivered to the balloon portion; placing the suture anchor into the cancellous bone while the balloon portion is in a deflated state and the at least one suture material extends from the cancellous bone through the compact outer layer of the bone; delivering a light curable adhesive to the balloon portion to expand the balloon portion from the deflated state to the inflated state, wherein the inflated diameter is greater than the diameter of the access hole; and activating a light source to deliver light to the light curable adhesive in the balloon portion to cure the light curable adhesive.

According to aspects illustrated herein, there is provided a method for attaching a soft tissue to a bone that includes forming an access hole in a bone, the access hole having a diameter and extending through a cortical bone into a cancellous bone; providing a suture anchor to the access hole, the suture anchor comprising at least one suture material and a balloon capable of expanding from a deflated state having a deflated diameter to an inflated state having an inflated diameter when a light curable adhesive is delivered to the balloon portion; placing the suture anchor into the cancellous bone while the balloon portion is in a deflated state and the at least one suture material extends from the cancellous bone through the compact outer layer of the bone; delivering a light curable adhesive to the balloon portion to expand the balloon portion from the deflated state to the inflated state, wherein the inflated diameter is greater than the diameter of the access hole; activating a light source to deliver light to the light curable adhesive in the balloon portion to cure the light curable adhesive; and attaching the soft tissue to the bone using the at least one suture material.

BRIEF DESCRIPTION OF THE DRAWINGS

The presently disclosed embodiments will be further explained with reference to the attached drawings, wherein like structures are referred to by like numerals throughout the several views. The drawings shown are not necessarily to scale, with emphasis instead generally being placed upon illustrating the principles of the presently disclosed embodiments.

FIG. 1A shows a balloon portion of the suture anchor in a deflated state. FIG. 1B shows a balloon portion of the suture anchor in an inflated state.

FIG. 1C shows an oblong base and suture material of the suture anchor. FIG. 1D shows a catheter and oblong base of the suture anchor.

FIG. 2A shows a perspective view of a suture anchor in a deflated state, the suture anchor having a single eyelet. FIG. 2B shows a perspective view of a suture anchor in an inflated state having a single eyelet. FIG. 2C shows a perspective view of a suture anchor in a deflated state, the suture anchor having two eyelets.

FIG. 3A shows a balloon portion of the suture anchor in a deflated state. FIG. 3B shows a balloon portion of the suture anchor in an inflated state.

FIG. 4A shows the catheter of the suture anchor having an illumination area. FIG. 4B shows a cross-sectional view of the catheter of the suture anchor.

While the above-identified drawings set forth presently disclosed embodiments, other embodiments are also contemplated, as noted in the discussion. This disclosure presents illustrative embodiments by way of representation and not limitation. Numerous other modifications and embodiments may be devised by those skilled in the art which fall within the scope and spirit of the principles of the presently disclosed embodiments.

DETAILED DESCRIPTION

Suture anchors and methods of using suture anchors for attaching soft tissue to bone are disclosed herein. The suture anchors disclosed herein have an expandable member. When in use, the suture anchor is placed in an access hole in a bone in a deflated state. The access hole may be just slightly larger than the diameter of the expandable member. Once in place, the expandable member is inflated and hardened such that the diameter of the expandable member is larger than the access hole. This results in a suture anchor with a high pull-out strength.

Figure 1A:
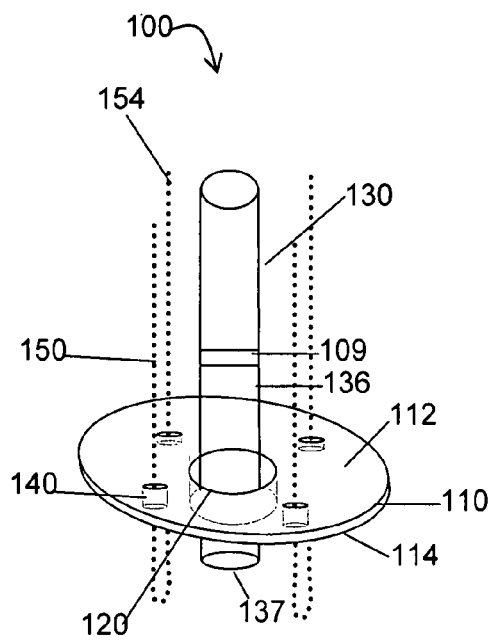
FIG. 1A and FIG. 1B show perspective views of a suture anchor of the presently disclosed embodiments.
Figure 1B:
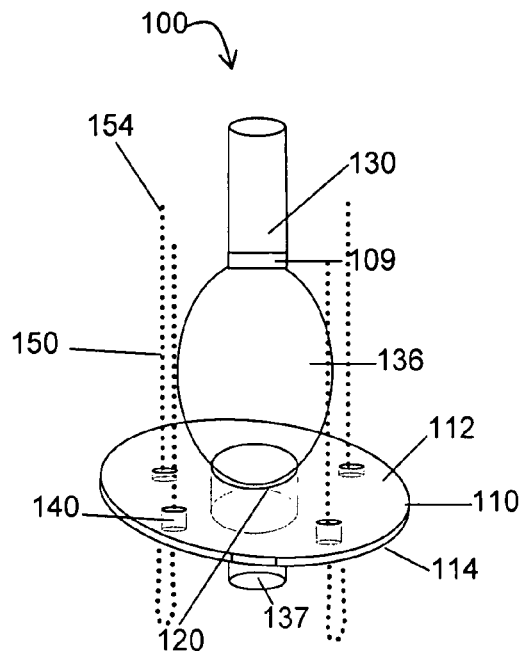

The main components of a suture anchor 100 are shown generally in FIG. 1A and FIG. 1B. The suture anchor 100 includes an oblong shaped base 110 having a top surface 112 and a bottom surface 114. A catheter 130 having an elongated shaft with a proximal end, a distal end, and a longitudinal axis therebetween runs through the base 110 through an oblong shaped center hole 120. The oblong shape of the center hole 120 allows for the base 110 to lay as flat as possible relative to the catheter 130. In an embodiment, the center hole 120 is radiused to reduce any stressors or sharp edges that may be present on the hole 120. The radiusing of the center hole 120 also results in an insertion side or a proper insertion direction to the base 110. The base 110 is free-floating around the catheter 130, thus allowing the base 110 to rotate relative to the catheter 130. In an embodiment, the base 110 is held on to the catheter 130 by a crimp in the catheter 130 diameter. In an embodiment, the base 110 is held on to the catheter 130 by an over sleeve that is larger than the hole 120 in the base 110, therefore precluding the base 110 from falling off of the catheter 130. The catheter 130 has at least one inner lumen capable of allowing a light cure adhesive to pass through. The distal end of the catheter 130 has a balloon portion 136 that inflates and deflates. The balloon portion 136 has at least one inner lumen capable of allowing a light cure adhesive to pass through. A separation area 109 is located at the junction between the balloon portion 136 and the catheter 130. A distal end 137 of the catheter 130 protrudes from the bottom surface 114 of the base 110. In an embodiment, the catheter 130 is formed of a pliable, resilient, conformable, and strong material, including but not limited to urethane, polyethylene terephthalate, nylon elastomer and other similar polymers. The balloon portion 136 engages the catheter 130 and is capable of expanding or inflating with the delivery of a light cure adhesive. In an embodiment, the light cure adhesive is a UV activated glue. The balloon portion 136, when expanded, may take on the following shapes: round, cylindrical, oval, rectangular or another shape. As shown in FIG. 1B, the balloon portion 136 is in the shape of an oval. The base 110 includes at least two eyelets 140, preferably four eyelets 140, for passage of a suture material 150. The suture material 150 may comprise pre-attached suture needles at a distal end 154 of the suture material 150 (the suture needles are not shown in the drawings).

Figure 1C:
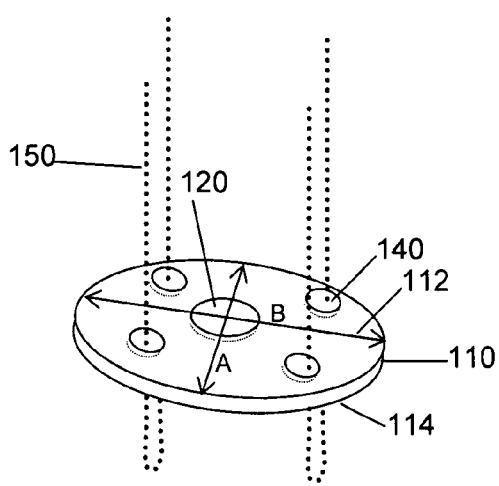
FIG. 1C and FIG. 1D show perspective views of some of the main components of a suture anchor of the presently disclosed embodiments.
Figure 1D:
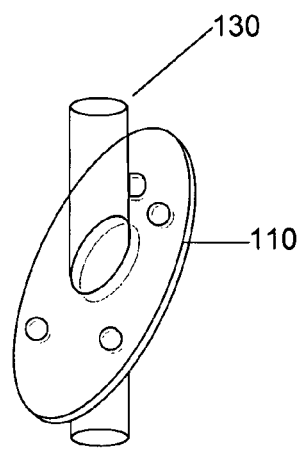

FIG. 1C shows a perspective view of the oblong base 110. The base 110 includes a short axis "A" and a long axis "B". The base 110 includes at least one pair of eyelets 140, preferably two pair of eyelets 140, for passage of the suture material 150. The suture material 150 is easily adjustable due to the fact that the suture material 150 passes from the top surface 112 to the bottom surface 114 of one eyelet 140 and then from the bottom surface 114 to the top surface 112 of another eyelet 140. This configuration makes it is easy to control the tension of each suture material 150. The design of the eyelets 140 allows for the pre-threaded suture material 150 to independently move when passing through soft tissue or during knot tying, reducing the risk of the suture material 150 from binding while facilitating suture management within soft tissue repair. In an embodiment, the oblong base 110 has dimensions of about 2 mm by about 8 mm. In an embodiment, the oblong base 110 has dimensions of about 3 mm by about 6 mm. Those skilled in the art will recognize that any oblong shape is possible for the base 110 as long as the shape is elongated in one direction, such that the shape is longer than it is broad. Other possible base shapes include, but are not limited to, rectangular or elliptical. When the catheter 130 is in a deflated state, the base 110 is able to rotate about the catheter 130, as shown in FIG. 1D. The base 110 is rotatable for easy insertion into a soft or hard tissue.

Figure 2A:
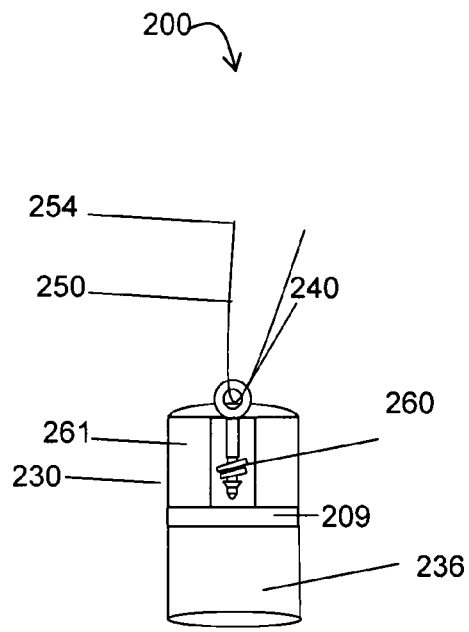
FIG. 2A, FIG. 2B and FIG. 2C show perspective views of a suture anchor of the presently disclosed embodiments.
Figure 2B:
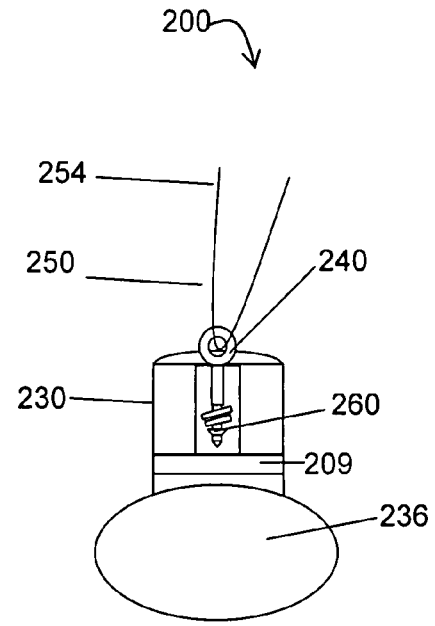
Figure 2C:
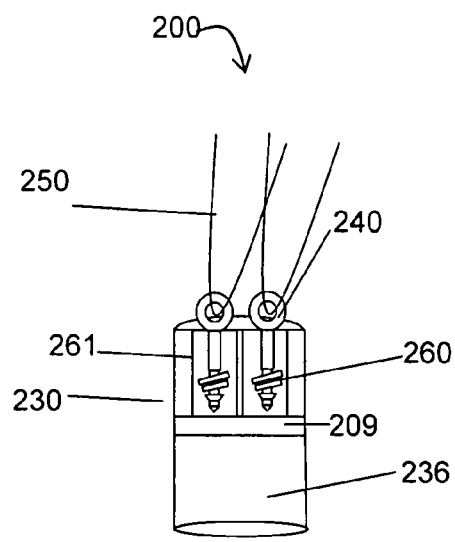
Figure 2D:
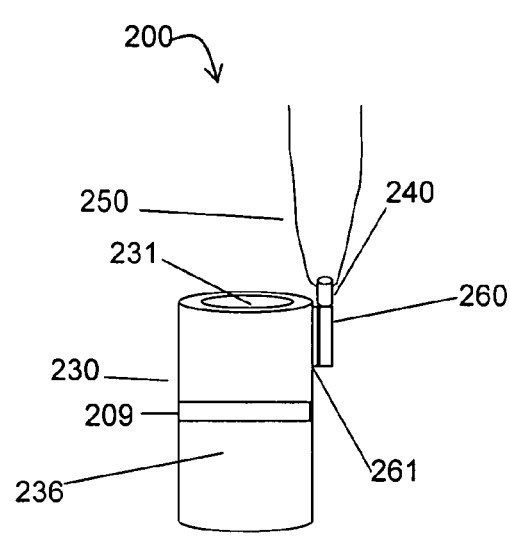
FIG. 2D shows a side view of the suture anchor of FIG. 2A.

FIG. 2A, FIG. 2B, FIG. 2C and FIG. 2D show views of an alternative embodiment of a suture anchor 200. In this embodiment, the suture anchor 200 includes a catheter 230 having an elongated shaft with a proximal end, a distal end, and a longitudinal axis therebetween. The catheter 230 has at least one inner lumen 231 capable of allowing a light cure adhesive to pass through. The distal end of the catheter 230 has a balloon portion 236 that inflates and deflates. A separation area 209 is located at the junction between the balloon portion 236 and the catheter 230. The balloon portion 236 is able to expand and inflate when a light cure adhesive is delivered to the balloon portion 236. In an embodiment, the light cure adhesive is a UV activated glue. The balloon portion 236, when expanded, may take on the shape of the bone cavity including, but not limited to, round, cylindrical, oval, rectangular or another shape. As shown in FIG. 2B, the balloon portion 236 is in the shape of an oval. At least one screw anchor 260 is positioned along the longitudinal axis of the catheter 230. The screw anchor 260 has at least one eyelet 240 on the top for passage of a suture material 250. The screw anchor 260 may be anywhere along the longitudinal axis of the catheter 230 and may be either inside or outside the catheter 230. There may be a plurality of screw anchors 260 on the catheter 230, as shown in FIG. 2C. As shown in the side view of the suture anchor 200 in FIG. 2D, the screw anchor 260 may be attached at the proximal end of one side of the catheter 230 by an attachment means 261. Those skilled in the art will recognize that there may be any number of screw anchors 260 on the catheter 230 and the screw anchor 260 may be anywhere along the catheter 230 and still be within the scope and spirit of the presently disclosed embodiments. The screw anchor 260 and the attachment means 261 may be fabricated from a polymer or a metal. The screw anchor 260, the attachment means 261 and the eyelet 240 may be fabricated as a single piece or as multiple pieces pined together. The suture material 250 may comprise pre-attached suture needles at a distal end 254 of the suture material 250 (the suture needles are not shown in the drawings).

Figure 3A:
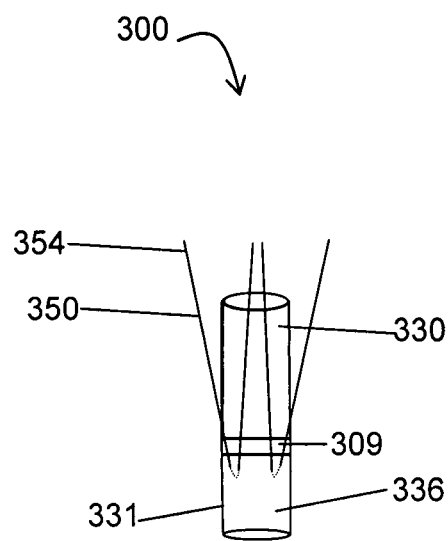
FIG. 3A and FIG. 3B show perspective views of a suture anchor of the presently disclosed embodiments.
Figure 3B:
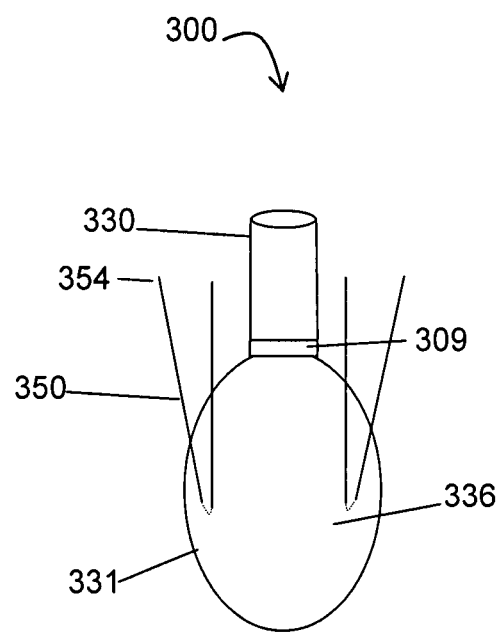

FIG. 3A and FIG. 3B show perspective views of an alternative embodiment of a suture anchor 300. In this embodiment, the suture anchor 300 includes a catheter 330 having an elongated shaft with a proximal end, a distal end, and a longitudinal axis therebetween. The distal end of the catheter 330 has a balloon portion 336 that inflates and deflates. A separation area 309 is located at the junction between the balloon portion 336 and the catheter 330. The catheter 330 has at least one inner lumen capable of allowing a light cure adhesive to pass through. The balloon portion 336 is able to expand and inflate when a light cure adhesive is delivered to the balloon portion 336. In an embodiment, the light cure adhesive is a UV activated glue. In an embodiment, at least one suture material 350 is embedded in a wall 331 of the balloon portion 336. The suture material 350 has limited ability to be maneuvered, tensioned or repositioned relative to the balloon portion 336. The suture material 350 may comprise pre-attached suture needles at a distal end 354 of the suture material 350 (the suture needles are not shown in the drawings). In an embodiment, the catheter 330 is formed of a pliable, resilient, conformable, and strong material, including but not limited to urethane, polyethylene terephthalate, nylon elastomer and other similar polymers. As shown in FIG. 3B, the balloon portion 336 expands to take the shape of an oval.

The suture anchors may engage any adhesive system known in the art that delivers a light cure adhesive. The adhesive system may engage at the proximal end of the catheter. Examples of adhesive systems include, but are not limited to, caulking gun type systems, syringe systems, bag systems that contain the adhesive where the delivery of the adhesive is controlled using a tube clamp or any other restrictor valve. In an embodiment, the balloon portion of the suture anchor is expanded from a deflated state to an inflated state using a delivery syringe of UV curable adhesive that is attached to a luer at the proximal end of the catheter. A control mechanism regulates the flow of the adhesive. The control mechanism of the syringe allows the adhesive to flow into the catheter and can stop the flow if desired. The delivery syringe makes direct contact to control the directional flow of the adhesive, and the direction of flow of the adhesive changes within the catheter in response to a change in the direction of the delivery syringe. In an embodiment, the delivery syringe prevents light from penetrating the outer surface of the syringe. Having an opaque syringe ensures that the adhesive contained in the delivery syringe is not exposed to light and will not cure in the syringe.

Figure 4A:
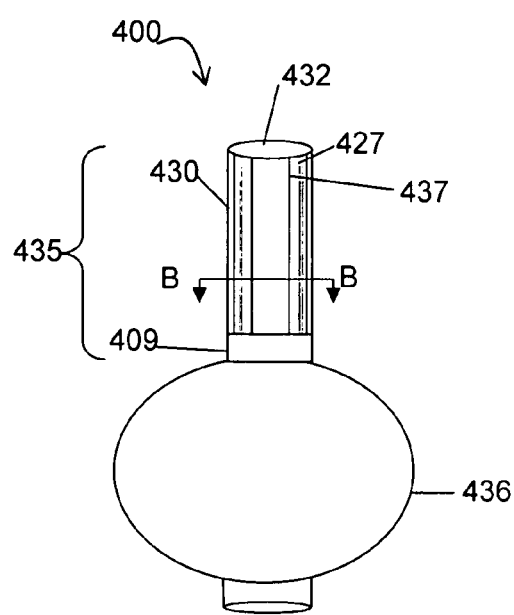
FIG. 4A and FIG. 4B show views of a catheter of a suture anchor of the presently disclosed embodiments.
Figure 4B:
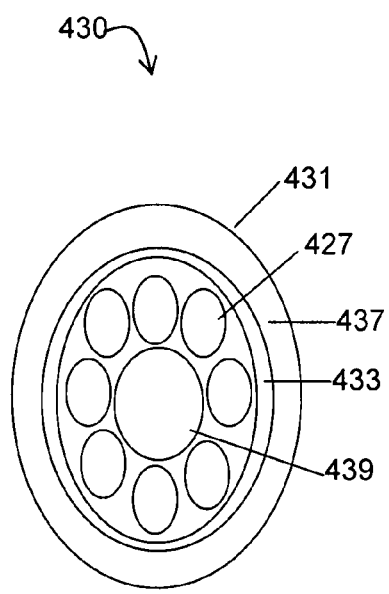

As shown in FIG. 4A, a catheter 430 of a suture anchor 400 includes a separation area 409 located at a junction between a balloon portion 436 and a proximal end 432 of the catheter 430. The separation area 409 may also be an illumination area 435. When activated, the illumination area 435 causes light to cure an adhesive located in the catheter 430 within the illumination area 435, as will be described below. The illumination area 435 also causes light to cure an adhesive located in the balloon portion 436. The illumination area 435 may include at least one light guide 437 which transmits light of the proper frequency to the illumination area 435 and provides sufficient light to cure the light curable adhesive. A cross-sectional view of the catheter 430 taken along line B-B is shown in FIG. 4B. The catheter 430 includes a catheter wall 431, a plurality of illumination fibers 427, a mechanical connector 433 for holding together the illumination fibers 427, and an inner lumen 439 through which a light curable adhesive is introduced. In an embodiment, the catheter 430 is the at least one light guide 437. In an embodiment, the at least one light guide 437 extends through the inner lumen 439 into the balloon portion 436 to guide a light into the balloon portion 436. The plurality of illumination fibers 427 are used to provide sufficient light to cure an adhesive. The mechanical connector 433 may include, but is not limited to, metallic rings, polymer rings, illumination rings, glue or similar structures. After the illumination fibers 427 are bound together, the illumination fibers 427 may be cut in an even manner. The illumination fibers 427 may be polished smooth to assist in pointing light illumination.

In an embodiment, an infusion catheter connects the at least one light guide 437 of the catheter 430 to a light source and precludes inadvertent or early activation of the light source (e.g., prior to the correct positioning and desired infusion amount of a light curable adhesive). The activation of the light source cures the adhesive that has been delivered to the balloon portion 436, resulting in the hardening of the inflated balloon portion 436. A cure refers to any chemical, physical, and/or mechanical transformation that allows a composition to progress from a form (e.g., flowable form) that allows the composition to be delivered through the catheter 430, into a more permanent (e.g., cured) form for final use in vivo. For example, "curable" may refer to uncured composition, having the potential to be cured in vivo (as by catalysis or the application of a suitable energy source), as well as to a composition in the process of curing (e.g., a composition formed at the time of delivery by the concurrent mixing of a plurality of composition components). The activation of the light source that is connected to the light guides 437 within the catheter 430 causes a complete cure of the adhesive to the point where the composition has been finally shaped for its intended use. By activating the light source, the light cure adhesive contained in the balloon portion 436 hardens. Activation of the light cure adhesive does not require a change in shape post activation; shrinking or swelling of the light adhesive after curing is limited or does not occur. In an embodiment, the catheter 430 of the suture anchor 400 may be constructed of illumination materials resulting in a light transmittable fiber catheter, which would not require illumination fibers 427 or light guides 437. In an embodiment, the at least one light guide 437 engages the light source. In an embodiment, the at least one light guide 437 is a flexible light pipe. The at least one light guide 437 directs light from a light source to the balloon portion 436. In an embodiment, a light taper is used to direct the light into the balloon portion 436 because the light source may be larger than the diameter of the catheter 430.

In an embodiment, the balloon portion 436 separates from a proximal end 432 of the catheter 430, allowing the balloon portion 436 to remain in a bone and the proximal end 432 of the catheter 430 to be more removed. After the adhesive in the balloon portion 436 is cured, such as by using the illumination fibers 427, the illumination area 435 may be activated causing light to cure any adhesive located in the catheter 430 within the illumination area 435. The illumination area 435 extends around the catheter 430 and has a stress concentrator. The stress concentrator may be a notch, groove, channel or similar structure that concentrates stress in the illumination area 435. The stress concentrator of the illumination area 435 may be notched, scored, indented, pre-weakened or pre-stressed to direct separation of the balloon portion 436 from the catheter 430 under specific torsional load. The separation area 409 ensures that adhesive does not leak from the proximal end 432 of the catheter 430 and/or the balloon portion 436. The separation area 409 seals the proximal end 432 of the catheter 430 and/or the balloon portion 436 and removes the proximal end 432 of the catheter 430 by making a break at a known or predetermined site (e.g., a separation area 409). The separation area 409 is located where the distal end of the catheter 430 meets the proximal end of the balloon portion 436 because the adhesive in the balloon portion 436 is hardened after activation of the illumination area 435. The separation area 409 may be various lengths and up to about an inch long. When torque is applied to the catheter 430 the catheter 430 separates from the balloon portion 436. Twisting the catheter 430 creates a torque sufficient in the separation area 409 to break the proximal end 432 of the catheter 430 from the balloon portion 436. The twisting creates a sufficient shear to break the residual adhesive and create a clean separation of the catheter/balloon interface. Because the adhesive in the separation area 409 has been cured and hardened by the illumination area 435, no adhesive can leak into the body from the proximal end 432 of the catheter 430 and/or the balloon portion 436.

The suture anchors of the presently disclosed embodiments may be inserted into a human patient's body at many different locations. The suture anchors may be inserted into either hard tissue (cartilage and bone) or soft tissue (generally, the ligaments, tendons, and muscles). In an embodiment, the suture anchors are inserted into bony tissue and are used to re-attach an associated tissue to the bone. The suture anchors of the presently disclosed embodiments may be used for a variety of medical procedures including, but not limited to, plastic surgery procedures, cosmetic procedures, and in surgical procedures involving repair of the knee, ankle, elbow, shoulder, and hand. It will be understood, however, that the methods and devices described herein are equally applicable to connecting detached tissue in other contexts as well.

Figure 5A:
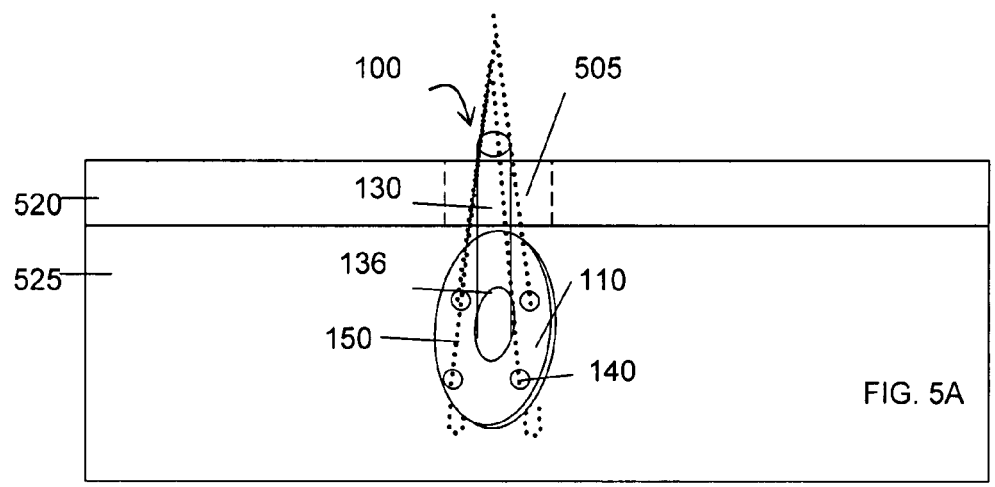
FIG. 5A, FIG. 5B and FIG. 5C show a close-up view of the method steps for placing a suture anchor of the presently disclosed embodiments into a bone.
Figure 5B:
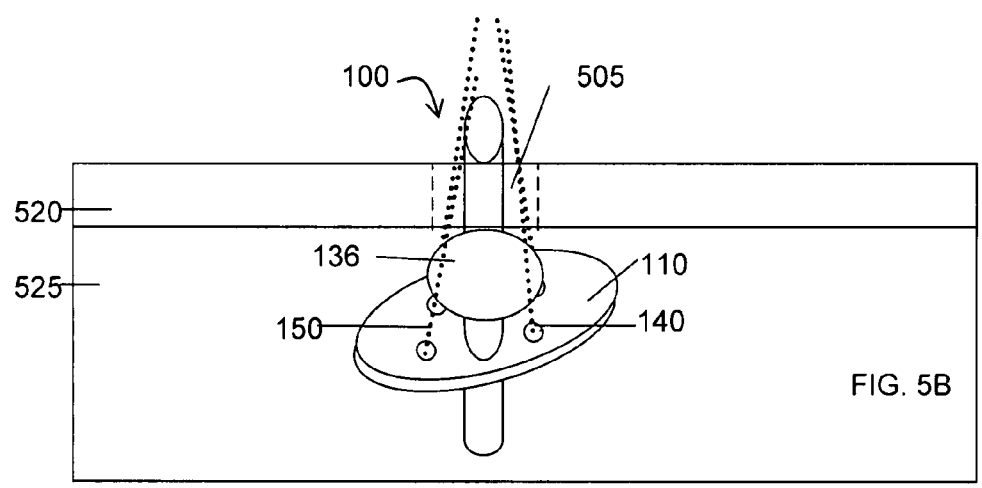
Figure 5C:
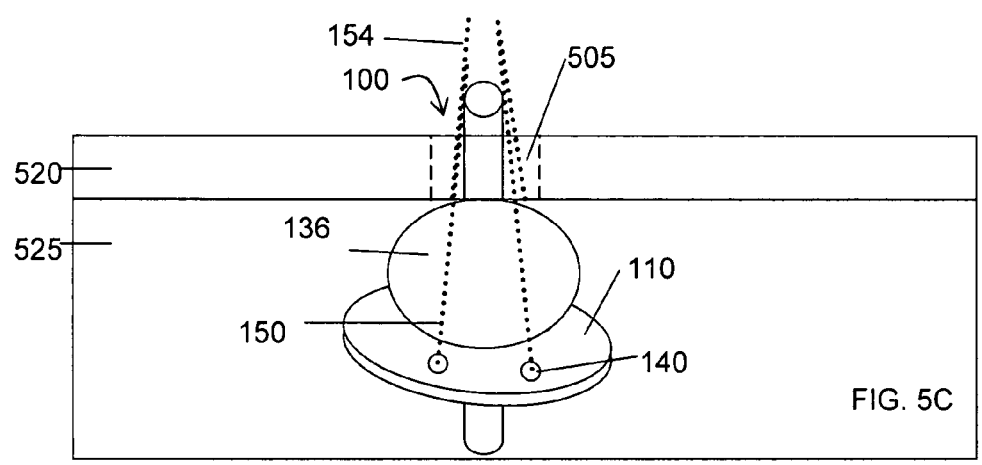

FIGS. 5A, 5B and 5C in conjunction with FIG. 1A, illustrate the method steps for inserting and expanding the suture anchor 100 in a bone tissue of a patient's body. The suture anchor 100 may then be used to engage an associated soft tissue to the bone. An access hole 505 is formed in the bone tissue of the patient's body by drilling or other methods known in the art. The access hole 505 is created such that the shorter axis "A" of the base 110 will fit through the diameter of the hole 505, with the longer axis "B" of the base 110 being about parallel to the axis of the hole 505. The access hole 505 extends through a hard compact outer layer 520 of the bone tissue into the relatively porous inner or cancellous tissue 525. In an embodiment, the access hole 505 has a diameter of about 3 mm to about 10 mm. In an embodiment, the access hole 505 has a diameter of about 3 mm. After the access hole 505 is drilled, the suture anchor 100 is inserted into the bone tissue such that the base 110 of the suture anchor 100 is positioned completely in the cancellous tissue 525 and a proximal end of a catheter 130 attached to the base 110 extends up and out through the compact outer layer 520. In an embodiment, the base 110 of the suture anchor 100 has dimensions of about 2 mm by about 8 mm. The suture anchor 100 may be placed within the access hole 505 using a sheath or similar surgical instrument known in the art. In an embodiment a sheath is used to insert the suture anchor 100 within the access hole 505. In an embodiment, the sheath is a thin walled tube which fits entirely around the suture anchor 100. Suture material 150 extends out of the bony tissue from at least one eyelet 140 of the base 110.

During the insertion stage, as shown in FIG. 5A, the catheter 130 is advanced and the sheath (not shown) is pulled back to expose the base 110 and the balloon portion 136. The base 110 is in an orientation such that the longer axis "B" of the base 110 is approximately parallel to the axis of the hole 505. Once the suture anchor 100 is in place within the bony tissue, the balloon portion 136 of the catheter 130 is inflated using a light curable adhesive, as shown in FIG. 5B. The expansion of the balloon portion 136 causes the base 110 to rotate and flatten out such that the long axis "B" of the base 110 becomes approximately perpendicular with the axis of the access hole 505. The base 110 has been rotated and flattened within the cancellous tissue 525. The balloon portion 136 of the suture anchor 100 is positioned against the base 110 at one end and against the inner surface of the compact bone layer 520 at the other end. The balloon portion 136 is inflated with an adhesive such that the balloon portion 136 becomes larger then the access hole 505 and as a result presents a large contact area against the inner compact bone layer 520, thus providing resistance to pulling out of the bone.

By activating a light source that is connected to the catheter 130, the adhesive may be cured, resulting in the hardening of the inflated balloon portion 136. Once the suture anchor 100 is in place, as shown in FIG. 5C, a medical professional may then approximate the free end of detached soft tissue to the surface of the bone tissue (not shown). By pulling up on the suture material 150, which extends out from the access hole 505, the inflated balloon portion 136 engages and conforms to the inner surface of the compact layer 520. As shown in FIG. 5C, the balloon portion 136, which may have an inflated diameter of from about 6 mm to about 8 mm is pushing up against an access hole 505 having a diameter of from about 3 mm to about 4 mm, thus the forces holding the suture anchor 100 in place are large. The suture anchor 100 resists pulling-out of the bone. The distal ends 154 of the suture material 150 may then threaded through soft tissue such as ligaments, tendons, muscles, skin and other soft tissue. The suture material 150 is then knotted and tied down to the bone surface. In this manner, various soft tissues may be engaged. Those skilled in the art will recognize that any of the suture anchors disclosed herein may be used with the method steps of FIG. 5.

When torque is applied to the catheter 130 the catheter 130 may be separated from the balloon portion 136. Twisting the catheter 130 creates a torque sufficient in a separation area of the catheter 130 to break a proximal end of the catheter 130 from the balloon portion 136. The twisting creates a sufficient shear to break any residual adhesive and create a clean separation of the catheter/balloon interface. Because the adhesive in the separation area has been cured and hardened by the illumination area, no adhesive can leak into the body from the proximal end of the catheter 130 and/or the balloon portion 136.

Figure 6:
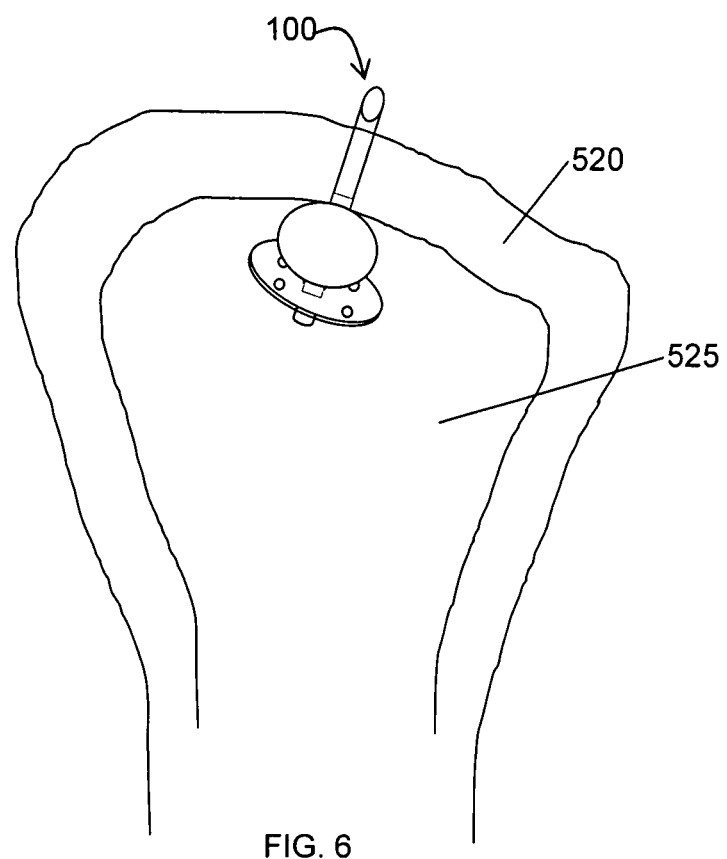
FIG. 6 shows an illustrative embodiment of a suture anchor in position in a bone.

FIG. 6 shows an illustrative view of the suture anchor 100 in position within a bone of a patient (suture material is not shown in this figure). In an embodiment, the balloon portion 136 separates from the catheter 130, allowing the balloon portion 136 to remain in the bone and the catheter 130 to be more easily removed, as described above.

The suture material 150 may be formed from conventional polymeric materials and may be absorbable or non-absorbable. Examples of non-absorbable suture materials include silk, polyethylene, polypropylene, polyvinylidene fluoride, polyesters and the like. Examples of absorbable suture materials include cat gut (collagen), aliphatic polyesters, lactide, glycolide, trimethylene carbonate, polycaprolactone, polydioxanone, and copolymers and blends thereof and the like. In an embodiment, the suture material 150 is a polyester material.

One or more radiopaque markers may be placed on the catheter and/or the balloon portion of the suture anchors of the presently disclosed embodiments. In an embodiment, the radiopaque marker is located at the transition point between the proximal end of the balloon portion and the distal end of the catheter. The radiopaque marker, using radiopaque material such as barium sulfate, tantalum, or other materials known to increase radiopacity, allows a medical professional to view the distal end of the catheter using fluoroscopy techniques. The radiopaque material provides visibility during inflation to determine the precise positioning of the balloon portion and/or catheter during placement and inflation. Once the correct positioning of the balloon portion and/or catheter is determined, the proximal end of the catheter may be attached to any adhesive system that contains a light cure adhesive.

All patents, patent applications, and published references cited herein are hereby incorporated by reference in their entirety. It will be appreciated that various of the above-disclosed and other features and functions, or alternatives thereof, may be desirably combined into many other different systems or applications. Various presently unforeseen or unanticipated alternatives, modifications, variations, or improvements therein may be subsequently made by those skilled in the art which are also intended to be encompassed by the following claims.

What is claimed is:

1. A suture anchor for attaching soft tissue to bone comprising:
   a free-floating base having a top surface, a bottom surface, a hole extending from the top surface to the bottom surface, and at least two eyelet holes extending completely through the base from the top surface to the bottom surface;
   a catheter positioned through the hole of the base, the catheter having an elongated shaft with a proximal end, a distal end, a longitudinal axis therebetween, and at least one inner lumen for a light curable adhesive to pass therethrough;
   a balloon portion engaging the catheter, wherein the balloon portion expands from a deflated state to an inflated state when the light curable adhesive is delivered to the balloon portion, wherein the catheter extends proximally and distally from the balloon portion; and
   a plurality of suture material passing through the eyelet holes to attach the soft tissue to the bone,
   wherein the free-floating base directly engages the balloon portion and is adapted to rotate relative to the catheter as the balloon portion expands from the deflated state to the inflated state.

2. The suture anchor of claim 1 wherein the suture material passes from the top surface to the bottom surface of a first eyelet hole and passes from the bottom surface to the top surface of a second eyelet hole.

3. The suture anchor of claim 1 wherein the light curable adhesive is a UV glue.

4. The suture anchor of claim 1 further comprising at least one light guide extending from the catheter into the balloon portion to guide a light from a light source into the balloon portion.

5. The suture anchor of claim 1 further comprising a light source for providing an ultraviolet light to the catheter.

6. The suture anchor of claim 1 further comprising a separation area allowing the catheter to be removed from the balloon portion.

7. The suture anchor of claim 1 wherein the balloon portion expands to an inflated state after being positioned within a cancellous tissue of the bone.

8. The suture anchor of claim 1 wherein the free-floating base has an oblong shape.

9. The suture anchor of claim 8 wherein the oblong shape base has dimensions of 2 mm by 8 mm.

10. A suture anchor for attaching soft tissue to bone comprising:
    a base having a top surface, a bottom surface, a hole extending from the top surface to the bottom surface, and at least two eyelets holes extending completely through the base from the top surface to the bottom surface;
    a catheter positioned through the hole of the base, the catheter including a lumen for passing a light cure adhesive into an expandable member portion of the catheter to inflate the expandable member portion, wherein the catheter extends proximally and distally from the expandable member portion;
    at least one light guide extending from the catheter into the expandable member portion to guide light into the expandable member portion; and
    a plurality of suture material passing through the eyelets holes to attach the soft tissue to the bone,
    wherein the base directly engages the expandable member portion so as to be rotated by the expandable member portion as the expandable member portion inflates.

11. The suture anchor of claim 10 wherein the base has an oblong shape.

12. The suture anchor of claim 11 wherein the oblong shape base has dimensions of 2 mm by 8 mm.

13. A suture anchor for attaching soft tissue to bone comprising:
    a rotatable oblong base having a top surface, a bottom surface, a central hole extending from the top surface to the bottom surface, and two pairs of eyelets holes extending from the top surface to the bottom surface;
    a catheter positioned through the central hole of the rotatable oblong base, the catheter including a lumen for passing a light cure adhesive into an expandable member portion of the catheter to inflate the expandable member portion, wherein the catheter extends proximally and distally from the expandable member portion; and
    a plurality of suture material passing between each of the pairs of eyelets holes to attach the soft tissue to the bone,
    wherein the rotatable oblong base directly engages the expandable member portion so as to be rotated by the expandable member portion as the expandable member portion inflate.

14. The suture anchor of claim 13 wherein the rotatable oblong base has dimensions of 2 mm by 8 mm.

15. The suture anchor of claim 13 wherein the expandable member portion of the catheter includes one or more radiopaque markers.

* * * * *